(12) United States Patent
Mahaffey

(10) Patent No.: US 6,295,867 B1
(45) Date of Patent: Oct. 2, 2001

(54) GEOLOGICAL SAMPLE SUB

(76) Inventor: Don F. Mahaffey, 8555 Laurens La. Apt #608, San Antonio, TX (US) 78218

(*) Notice: Subject to any disclaimer, the term of this patent is extended or adjusted under 35 U.S.C. 154(b) by 0 days.

(21) Appl. No.: 09/469,183

(22) Filed: Dec. 21, 1999

Related U.S. Application Data

(60) Provisional application No. 60/113,351, filed on Dec. 21, 1998.

(51) Int. Cl.$^7$ .................................................. G01N 1/00
(52) U.S. Cl. ................................. 73/152.02; 73/864.73; 73/863.23
(58) Field of Search ........................... 73/863.23, 864.73, 73/152.02, 152.23–152.25, 152.28; 166/254.2, 264; 175/58–60

(56) References Cited

U.S. PATENT DOCUMENTS 3,123,157 * 3/1964 Graham .
3,427,653 * 2/1969 Jensen .

* cited by examiner

*Primary Examiner*—Robert Raevis
(74) *Attorney, Agent, or Firm*—Peter A. Borsari

(57) ABSTRACT

A sturdy tubular "sub" apparatus for collecting geological samples (Geological Sample-Sub or GSS) that may be entrained within a conventional drill string apparatus for conducting a drill-stem-test. The apparatus may be manufactured from conventional drill-collar stock and may be provided threads at each end of a standardized thread size so that it may be readily exchanged with or attached to other subs comprising the drill string apparatus. The drill string apparatus with the incorporated GSS may be lowered in a closed and empty state into a drilled hole whereupon it is packed off and the apparatus may be opened. A slit-like opening in the GSS permits entry of rock samples into the tubular apparatus, whereas baffles located within the apparatus near both ends prevent the escape of the samples as fluid in the hole rushes through the open drill string assembly.

6 Claims, 3 Drawing Sheets

FIG. 5
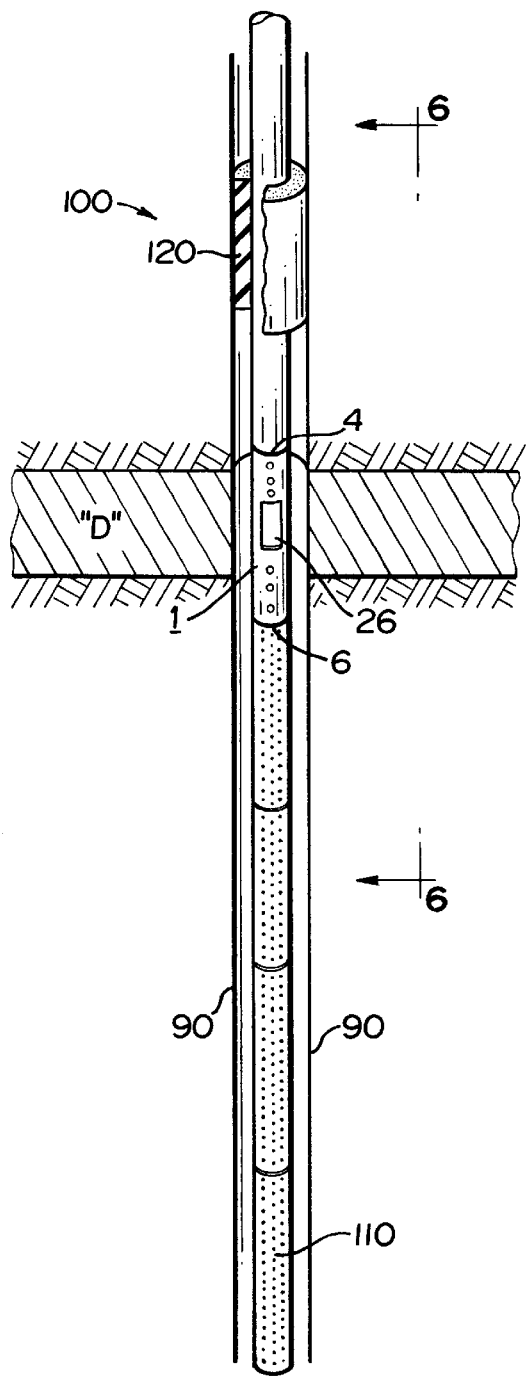
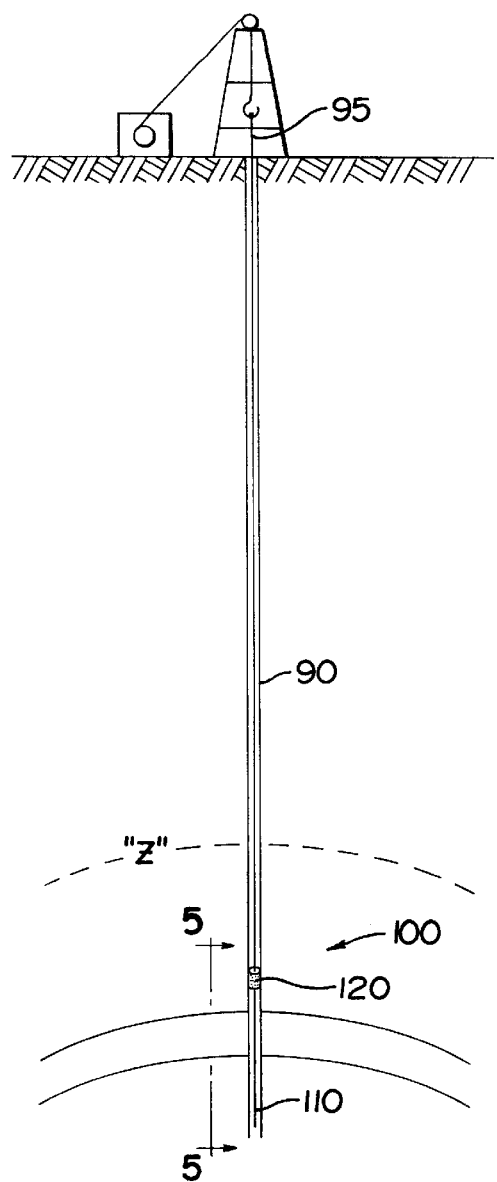
FIG. 4

GEOLOGICAL SAMPLE SUB

RELATED APPLICATIONS

This application claims the benefit of priority under 35 U.S.C. §119(e) from Provisional Application for Patent No. 60/113,351 filed in the United States Patent & Trademark Office on Dec. 21, 1998.

FIELD OF INVENTION

This invention relates to a new and novel apparatus for facilitating testing of geological samples within a hole drilled into the earth comprising a tubular body formed from thick-walled tubular pipe and having a slit therein whereby rocks motivated by fluid movement may enter into the tubular body. Baffles at either end of the tubular body prevent the rocks from exiting the tubular body until it is desired to remove and examine them.

BACKGROUND OF THE INVENTION

When bores are made into the earth for the purpose of obtaining fossil fuels such as oil and hydrocarbon gases, it is desirable to obtain and examine geological samples comprising rock cuttings or chips. From the samples obtained, a trained observer can elucidate whether hydrocarbons are present and also determine the lithic nature, kind and type of the subterranean reservoir containing the hydrocarbons. Current methods for obtaining these samples include vertical coring using drill pipe and appropriate coring equipment as well as side-wall horizontal coring methods such as explosive processes or other mechanical processes.

Under normal conditions, the bottom-hole pressure in a bore or hole drilled into the earth increases predictably at the rate of from 0.434 lb./s.i. to 0.450 lb./s.i. per foot of depth. For example, a hole drilled to 1000 feet will have a bottom-hole pressure in the range of from 434 to 450 p.s.i. The method of using the Geological Sample-Sub (GSS) of the current invention exploits this bottom-hole pressure at a drilled depth to implode the surrounding rock. Rock dislodged by this implosion may be passively caught and retained by the GSS until it is desired to remove and examine it to determine its lithic nature and/or hydrocarbon content. Moreover, the GSS achieves the goal of capturing the desired rock sample without impeding the flow of fluids and gases through an associated string assembly having attendant testing apparatus.

SUMMARY OF THE INVENTION

Accordingly, it is an object of the present invention to provide a geological sample sub which may be utilized with conventional drilling apparatuses, being suitable for incorporation and joinder with these apparatuses and being capable of capturing and retaining rock samples in a passive manner.

It is another object of the present invention to provide a geological sample sub which is sturdy, having no moving parts and comprising a unitary piece of equipment.

It is an additional object of the present invention to provide a geological sample sub which is easily assembled from materials which are readily available and known within the drilling art.

It is a further object of the present invention to provide a geologic sample sub that presents an economic use of material and which is simple in its design.

Additional objects, advantages and novel features of the present invention will be set forth in part in the description which follows and in part will become apparent to those skilled in the art upon examination of the following specification or may be learned by practice of the invention. To the accomplishment of the above-related objects, this invention may be embodied in the forms illustrated in the accompanying drawings, attention being called to the fact, however, that the drawings merely are illustrative, and that changes may be made in the specific construction illustrated and described within the scope of the appended claims.

BRIEF DESCRIPTION OF THE DRAWINGS

The present invention will be better understood with reference to the appended drawing sheets, wherein:

FIG. 4 is a cross-sectional environmental perspective view of the geologic sample sub of the instant invention.

FIG. 5 is a cross-sectional environmental perspective view of the geologic sample sub of the instant invention showing a magnified view of the region shown in FIG. 4 and bounded by line A–A'.

DETAILED DESCRIPTION

Figure 3:
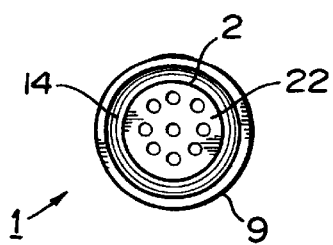
FIG. 3 is a top view of the geologic sample sub of the instant invention.
Figure 1:
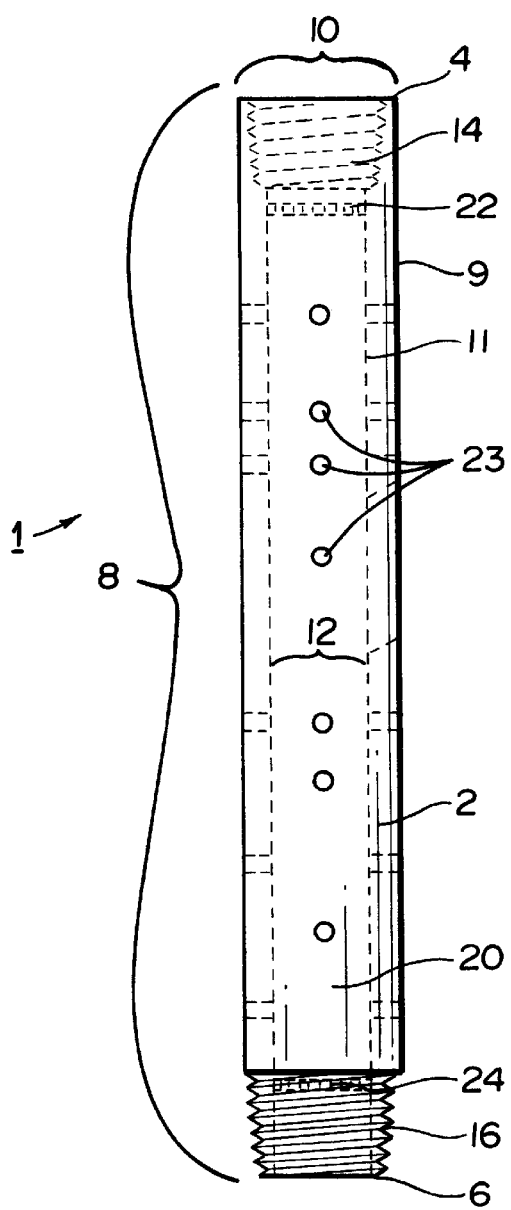
FIG. 1 is a front cross-sectional view of the geologic sample sub of the instant invention.
Figure 2:
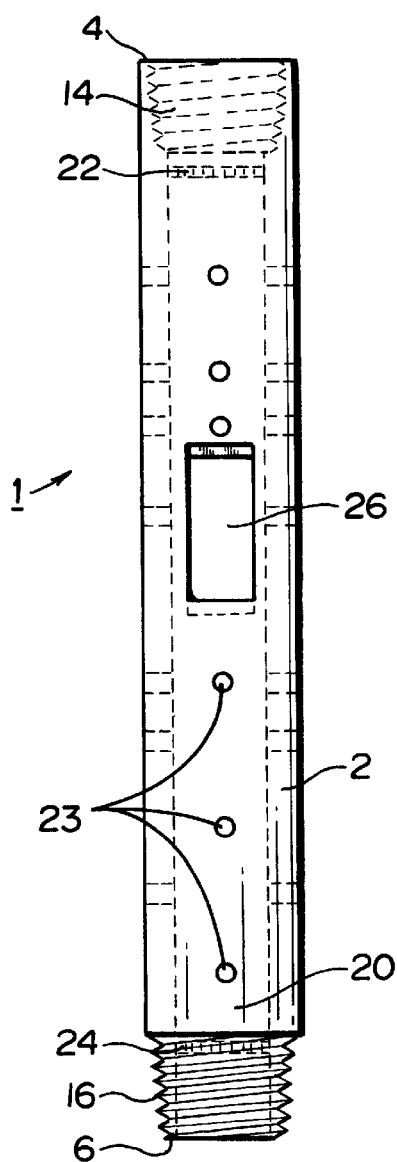
FIG. 2 is a side cross-sectional view of the geologic sample sub of the instant invention.
Figure 6:
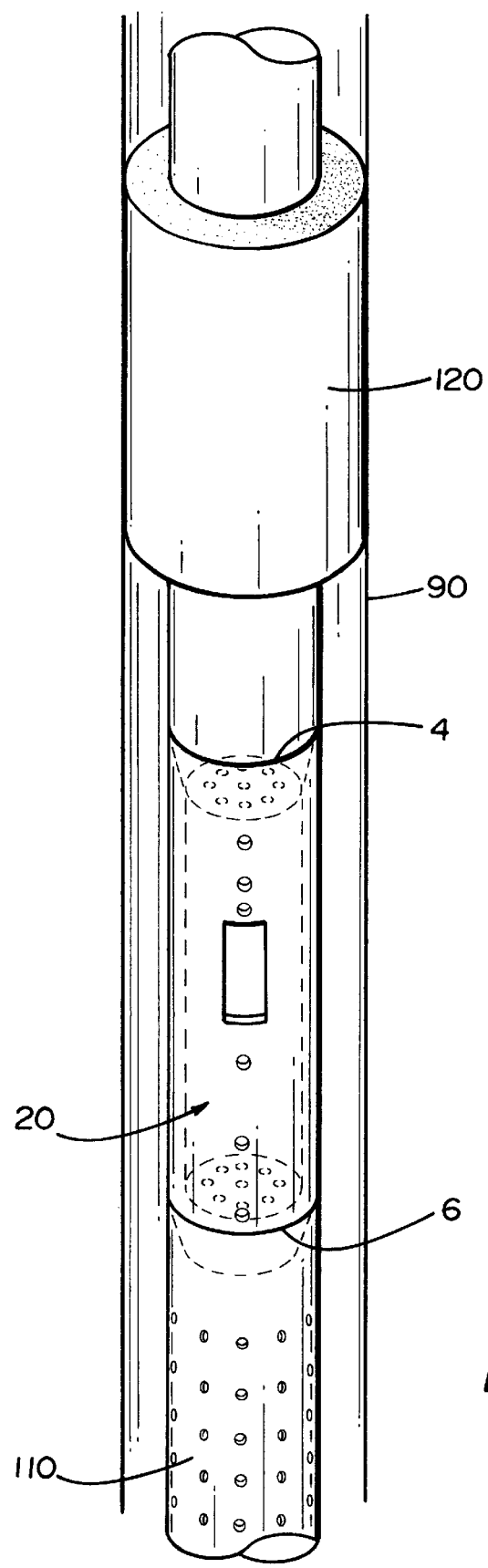
FIG. 6 is a cross-sectional environmental perspective view of the geologic sample sub of the instant invention showing a magnified view of the region shown in FIG. 4 and bounded by line B–B'.

The present invention relates to an apparatus for collecting geologic samples from a drilled hole which is attachable to conventional drill string assemblies. The apparatus is a "sub" apparatus which acts in conjunction with the other components that form the string assembly. As shown in FIGS. 1 through 3, the Geological Sample-Sub (GSS) 1 comprises a tubular body 2 surrounding a passageway 20 and having a first end 4, a second end 6, a length 8, an outer surface 9 with outer diameter 10 and an inner surface 11 with inner diameter 12. The GSS may be constructed from any conventional drill-collar stock—thick walled tubular pipe having relatively standardized inner and outer diameters— so that the GSS can be used compatibly with commonly used and available tubular goods for drilling holes. Typically, the GSS would be of some standardized length 8 of approximately 5 feet, but can be of other pipe lengths as needed. At this standardized length, tubular pipe is available having relatively standardized outer diameters of 2.375", 3.375" and 5.0" which are suitable as an outer diameter 10 of the GSS. Respective inner diameters with pipe having these outer diameters can vary from one manufacturer to another, but suitable pipe is readily available for the GSS having an outer diameter 10 of 5.0" and having an inner diameter 12 of approximately 2.375". The tubular body 2 should be free of upsets along its length 8 and if any tool joints are present, they should be flush joints.

At the first end 4 of the tubular body 2 along the inner surface 11, a joining means comprising female threads 14 is provided to form a "box". At the opposing second end 6 along the outer surface 9, a joining means comprising male threads 16 is provided to form a "pin". Although disposed at opposing ends of the tubular body, the male and female threads may be fabricated so as to be in mating fashion, both having a standard thread size of 3.5 A.P.I. which is a standard within the oil industry. When fabricated in this fashion, the GSS may be connected to other oil industry drill apparatus interchangeably and at either first end 4 or second end 6.

A plurality of perforations or holes 23 having a diameter of approximately 0.375" to 0.50" perforate the length of the GSS 1 at 6.0" intervals from the inner surface 12 of the tubular body 2 to the outer surface 9; the sets of holes are radially displaced from one another about the tubular body, thereby creating a fluid pathway joining the fluid passage way 20 to the exterior space lying outside of the GSS. In use, this exterior space would comprise the space between the GSS and the walls of a wellbore, drilling hole or the like. The tubular body also is perforated with at least one slit 26 which is made toward the first end 4 and which defines a rectangular window of about 10" in length and about 2" in width. Additional slits may be provided depending upon the size of the tubular body and strength of the material from which it is made.

A first baffle plate 22 is joined to the inner surface 11 of the tubular body 2 proximate to the first end 4; similarly, a second baffle plate 24 is joined to the inner surface proximate to the second end 6. Each of the baffle plates comprises a perforated metal disc which may be welded to the inner surface of the tubular body so that each disc becomes integral with this surface and is permanently attached thereto. Alternatively, the baffle plate may be constructed to be changeable or removable.

As described above, the GSS is a simple apparatus lacking moving parts and comprising a unitary metal tube having numerous perforations, joining means, baffle means and a central passageway through which fluid may flow.

Turning now to FIGS. 4 and 5, the GSS is shown in the field, whereat it may be desirable to conduct a drill-stem-test (DST) in a drilled zone, rock layer or formation "Z" which is suspected to contain or produce hydrocarbons. A typical DST bottom-hole assembly 100 may consist of a desired length of flush-joint perforated pipe 110 to which is attached a packer tool 120 consisting of a length of pipe covered by a deformable rubber sheath which can sealingly impinge upon the walls of a drill hole 90. Ancillary tools such as pressure gauges, fluid recovery sample container, circulating subs, down-hole jars, back-off sub, temperature gauges and the like are attachable above the packer tool. Components of the assembly are provided with joining means essentially analogous to the male and female threads 14 and 16 so that each component of the assembly 100 including the GSS 1 may be joined to another by a simple screwing maneuver. Ultimately, the assembly 100 is screwed onto a drill stem 95 before it is lowered into the drilled hole 90. The GSS 1 may be included in the assembly by screwing it into the DST assembly 100 such that when the assembly is lowered into the bottom of the drill hole 92, the GSS is located within the depth range "D" which is of interest; e.g. if it is desirable to obtain a sample from a depth of 30 feet to 40 feet above the bottom of the hole, the GSS is positioned within the assembly so that it will be resident in the hole above 30 to 40 feet of flush-joint perforated pipe 110 (the "tail-pipe") which forms the bottom end of the DST assembly 100.

The DST assembly 100 is "closed" when lowered into the bole, such that fluid flow through the assembly is either prevented or minimized. When the GSS 1 is positioned in the hole 90 at the desired depth, the packer tool 120 is set very tightly against the walls of the hole to "pack-off" the hydraulic/hydrostatic weight of drilling mud located above the packer tool in the drill hole outside the drill pipe/DST assembly. Thus, the closed DST assembly and the overlying drill stem 95 are devoid or nearly-devoid of fluid when originally lowered into the hole. Fluids and gases present in the hole 90 exert a pressure to the exterior of the assembly due to hydraulic/hydrostatic effects but cannot readily enter the assembly in the closed state. Consequently, opening the the assembly within the surrounding zone Z creates a large and immediate pressure differential at the lower portion of the drill hole 90 such that an implosion of the walls of the hole occurs. Any fluids or gasses 130 contained in the zone Z of interest leave the zone, enter the perforated tail pipe 110, and proceed upwards through the GSS 1 and packer 120 interiors and through the various measuring devices and the remainder of the drill stem 95.

Rock samples dislodged in the implosion may enter the passageway 20 of the GSS 1 through the slit 26 wherein they are trapped. Fluid flowing upwards through the GSS will force the samples to impinge upon the first baffle plate 22 whereat they are halted from progressing further upward into the string assembly. As the pressure differential within the string assembly drops off and fluid flow ceases or reverses, the rock samples are prevented from dropping out of the tubular body 2 of the GSS by the screening action of the second baffle plate 24. Notwithstanding the presence of these rock samples within the GSS, the perforations in both of the baffle plates permits fluid flow to be relatively unimpeded through the string assembly. When the DST assembly 100 is removed from the drilled hole 90, the rock sample collected by the GSS 1 may be examined.

While particular embodiments of the invention have been described, it will be understood, of course, that the invention is not limited thereto, and that many obvious modifications and variations can be made, and that such modifications and variations are intended to fall within the scope of the appended claims.

What is claimed is:

1. A tubular device to collect geological samples from a conventional drilling assembly comprising:

a hollow tubular body having an outer surface, an inner surface and a passageway running therethrough;

an open first end having female threads disposed on said inner surface;

an open opposite second end having male threads disposed on said outer surface, a plurality of perforations passing from said inner surface to said outer surface;

at least one slit opening passing from said inner surface to said outer surface;

a first baffle plate in the form of a perforated metal disc which is joinable to said inner surface of said tubular body proximate to said first end; and a second baffle plate in the form of a perforated metal disc which is joinable to said inner surface of said tubular body proximate to said second end, wherein said female threads and said male threads are configured in such a manner that said tubular device is readily connectable to a conventional drilling assembly.

2. The tubular device in accordance with claim 1, wherein each of said plurality of perforations has a diameter of about 0.375 inches to about 0.50 inches.

3. The tubular device in accordance with claim 1, wherein said plurality of perforations are disposed at about 6.0 inch intervals along said hollow tubular body and are radially displaced from one another about said tubular body.

4. The tubular device in accordance with claim 1, wherein said at least one slit opening is in the form of a rectangular window of about 10.0 inches in length and about 2.0 inches inches in width.

5. The tubular device in accordance with claim 1, wherein said hollow tubular body has an outer diameter of about 5.0 inches, an inner diameter of about 2.75 inches and a length of about 5.0 feet.

6. A method for collecting geologic samples from a wellbore using the tubular device in accordance with claim 1, comprising the steps of:

joining said female threads of said first end of said tubular device to a corresponding male threaded end of a conventional drill string component and joining said male threads of said second end of tubular device to a corresponding female threaded end of a conventional drill string component in order to form a resulting drilling assembly having said tubular device entrained therein;

lowering said resulting drilling assembly into a wellbore in a closed configuration such that fluid flow through said assembly is prevented or minimized;

packing off the drilling hole with a packer assembly; and opening said resulting drilling assembly such that a large pressure differential between the interior of said resulting drilling assembly and the surrounding wellbore creates an implosion of the walls of the wellbore and a fluid flow is enabled from the wellbore into and through said resulting drilling assembly and said tubular device, whereby rock samples contained within the fluid flow entering said tubular device through said slit opening become entrapped between said first and second baffles of said hollow tubular body thereby providing said geologic samples.

* * * * *